(12) United States Patent
Levkovitz

(10) Patent No.: US 6,652,461 B1
(45) Date of Patent: Nov. 25, 2003

(54) ULTRASOUND DEVICE FOR THREE-DIMENSIONAL IMAGING OF INTERNAL STRUCTURE OF A BODY PART

(75) Inventor: Zeev Levkovitz, Raanana (IL)

(73) Assignee: F.R.A.Y Project Ltd., Herzliya (IL)

( * ) Notice: Subject to any disclaimer, the term of this patent is extended or adjusted under 35 U.S.C. 154(b) by 0 days.

(21) Appl. No.: 09/958,828

(22) PCT Filed: Apr. 14, 2000

(86) PCT No.: PCT/IL00/00223

§ 371 (c)(1),
(2), (4) Date: Jan. 22, 2002

(87) PCT Pub. No.: WO00/62677

PCT Pub. Date: Oct. 26, 2000

(30) Foreign Application Priority Data

Apr. 15, 1999 (IL) ................................................. 129461

(51) Int. Cl.[7] ................................................. A61B 8/00
(52) U.S. Cl. .................... 600/443; 600/459; 128/916
(58) Field of Search ............................. 600/407–471, 600/493; 73/570–648; 367/117, 119–129, 153, 157, 173, 174, 180; 29/25.35, 594; 381/150, 151, 337–354, 173, 190; 128/916

(56) References Cited

U.S. PATENT DOCUMENTS

| | | |
|---|---|---|
| 3,906,937 A * | 9/1975 | Aronson ..................... 600/493 |
| 4,074,564 A | 2/1978 | Anderson |
| 4,206,653 A | 6/1980 | LeMay |
| 4,625,555 A | 12/1986 | Fujii |
| 4,662,222 A * | 5/1987 | Johnson ....................... 73/602 |
| 5,235,857 A | 8/1993 | Anderson |
| 5,435,312 A | 7/1995 | Spivey et al. |

FOREIGN PATENT DOCUMENTS

FR 2 477 404 2/1981

* cited by examiner

Primary Examiner—Ali M. Imam
(74) Attorney, Agent, or Firm—Browdy and Neimark, P.L.L.C.

(57) ABSTRACT

Ultrasound-based imaging device and software operated method are presented for monitoring a body part generating data indicative of a three-dimensional image of an internal structure of the body part. The device is portable and comprises a substantially elastic cover for covering the body part, wherein the cover is coupled to a control unit and is connectable to a computer device. The cover carries an array of ultrasonic transceivers, each of a kind emitting a beam of ultrasonic waves for irradiating an area within a region covered by the cover, and detecting signal response of the irradiated area. The transceivers are arranged in at least two spaced parallel groups. The transceivers of each group are arranged in a spaced-apart relationship, the space between each two adjacent transceivers in the group being such that an overlap exists between the areas irradiated by the adjacent transceivers.

9 Claims, 4 Drawing Sheets

US 6,652,461 B1

ULTRASOUND DEVICE FOR THREE-DIMENSIONAL IMAGING OF INTERNAL STRUCTURE OF A BODY PART

REFERENCE TO RELATED APPLICATIONS

The present application is the national stage under 35 U.S.C. 371 of international application PCT/IL00/00223, filed Apr. 14, 2000 which designated the United States, and which international application was published under PCT Article 21(2) in the English language.

FIELD OF THE INVENTION

The present invention is in the field of imaging techniques, and relates to ultrasound imaging device for monitoring an organ of a patient and displaying an image of its internal structure.

BACKGROUND OF THE INVENTION

Ultrasound-based imaging techniques are known and widely used for observing organs, in the human body for medical diagnosis. Some ultrasound systems utilize a hand-held probe containing an array of transducers that convert electrical signals into ultrasonic waves, and appropriate signal reception means. The probe is appropriately placed on the patient's body and an ultrasound beam is directed towards a location within the region of interest. To image the entire region, the probe is displaced with respect to the body thereby providing the scanning of the region. This enables to construct a two-dimensional image of the region.

Various methods and devices have been developed aimed at improving the performance of ultrasound imaging systems, and are disclosed, for example, in the following U.S. Pat. Nos. 4,625,555; 5,235,857; and 5,435,312.

U.S. Pat. No. 4,625,555 discloses a measurement apparatus utilizing three ultrasonic transducers wherein first and second transducers are arranged opposite to each other across an object interposed therebetween, and a ray from the third transducer intersects a ray connecting the first and second transducers. The second transducer receives ultrasonic waves emitted by the first and third transducer after corresponding time periods, and the first transducer receives an ultrasonic wave emitted by the third transducer after a respective time interval. On the basis of these time periods, a distribution of propagation velocity of sound internally of the object is measured.

U.S., Pat. No. 5,235,857 discloses a real-time 3D medical ultrasound imaging machine, wherein either a single transducer or a two-dimensional array of transducer is associated with an array of receivers. A body to be imaged is located outside a plane defined by the transducer(s) and receivers.

U.S. Pat. No. 5,435,312 discloses an acoustic imaging device, in which several transducer and detector means are arranged in a ring so as to at least partly encircle a body to be imaged. Each of the transducers is operated for transmitting signals with subsequent reception of scattered waves by remaining transducers. This technique enables the imaging of a single slice of the organ.

SUMMARY OF THE INVENTION

There is accordingly a need in the art to facilitate real-time 3D imaging with ultrasonic radiation, by providing a novel method and device for ultrasound-based imaging.

The device according to the invention, in distinguish to the conventional devices of the kind specified, has a simple and portable construction, and is easy to operate (generally similar to the known blood-pressure measuring device). This enables the use of the device for the immediate monitoring of an injured patient in outdoor conditions or at the patient's home. To this end, the device is connected to a conventional computer, for example a portable computer (laptop), typically available at the user's home, ambulance, physician's office, or hospital. The computer device is installed with a predetermined software application capable of processing data coming from the imaging device. This image processing does not require a complicated sampling procedure, due to the specific arrangement of transceivers provided in the imaging device.

The term "transceiver" signifies a unit composed of a transmitter of radiation (of ultrasonic waves in this case) and a detector (receiver) of returned radiation.

The main idea of the present invention is aimed at 3D mapping of an internal structure of a body part, and is based on the provision of an array (matrix) of transceivers mounted on an elastic cover for covering or wrapping a patient's organ (limb) when putting the device in operation. The transceivers are arranged in spaced parallel groups, each group including several spaced-apart transceivers. Each pair of adjacent transceivers in the group (which form a circle when in an operative position of the cover) provides stereoscopic imaging of an area within the entire region imaged by all the transceivers. Consequently, each such group of transceivers provides a 360-degree section image of the organ, at least two groups of transceivers being thereby sufficient for constructing a three-dimensional image of the structure performing a data processing procedure by the software application. The transceivers are connected to a control unit, which is operated by the software application for electrically operating the transceivers in a predetermined manner. By coupling output circuits of the transceivers to the computer device, either directly, or through a communication link, data coming from the transceivers is processed and a 3D image is constructed and displayed on a monitor of the computer device.

The image can be stored in the memory of the computer, thereby enabling to detect changes in the internal structure of the patient's body part, that may be caused by drugs, as well as enabling the timely detection of blood thromboses.

The transceivers transmit and receive signals in accordance with the following parameters predefined by the software application: timing (sequence), signal intensity and pulse duration. The software application, in response to data coming from the transceivers, processes data indicative of the collected samples and determines whether the collected data is sufficient for constructing the 3D image of the structure. If the received data is insufficient the software application operates the transceivers for further collection of samples until the complete 3D image can be constructed.

There is thus provided according to one broad aspect of the present invention, an imaging device for monitoring a body part and generating data indicative of a three-dimensional image of an internal structure of the body part, the device comprising:

(i) a substantially elastic cover for covering the body part when in an operative position of the device;

(ii) a control unit coupled to the cover;

(iii) an array of ultrasonic transceivers mounted on the cover each for emitting a beam of ultrasonic waves for irradiating an area within a region covered by the cover, and for detecting a signal response of the irradiated area, the array of the transceivers being composed of at least two spaced-apart parallel groups of the transceivers, wherein the transceivers of each group are arranged in a spaced-apart relationship, and the space between each two adjacent transceivers in the group is such that an overlap exists between the areas irradiated by the adjacent transceivers.

The cover when in an inoperative position thereof may be in the form of a circle so as to form a spherical part when in the operative position thereof This is design of the cover may be applied to a woman's abdomen or breast. The cover may be in the form of an open sleeve provided with two fasteners at its opposite ends for securing the cover on the body part wrapped by the cover. The cover may be in the form of sleeve (cuff) open at opposite ends so as to put onto the body part.

Generally speaking, the device according to the present invention provides for acquiring 2D images of the sections, and creating a 3D structure of the inside of the body part (limb). The 3D image will be presented on a conventional PC monitor or a laptop monitor. Generally, the image can be displayed in a regular way (i.e., on the computer monitor), or by virtual reality or holograms-based technique. Additionally, the obtained picture (3D image) can be rotated on the display by simply operating a computer mouse or the like. The use of the flexible cover allows the system high mobility in emergencies, either in the field or at the scene of an event.

The present invention enables examination (monitoring) without having to move the patient (in severe accidents), and enables the accurate and reliable reporting of the severity of the injury in the field. The use of 3D display, spatial display or any other conventional monitor enables certain rapid identification of types and natures of fractures within limbs, without the need for prior surgical intervention. The present invention can be used for the identification of blood vessels and their location, and the introduction of a needle for purposes of IV, blood testing, etc., and is assured to locate the vein on the first attempt. The present invention enables early identification of irregularities in the limbs and in the anatomical or tissue structure of the internal array, without surgical intervention.

The invention can be advantageously useful for monitoring the health condition of an injured patient in outdoor conditions or at the patient's home, e.g., for monitoring osteoporosis, arteriosclerosis or tumors, and for taking blood samples. Specifically, the present invention provides a facile method and a flexible device for monitoring changes in a patient's organ so as to monitor significant parameters of the patient's health. Further, such a device may be used for treating injured soldiers in battle when the mobility and the compactness of the device are of great importance.

According to another aspect of the present invention, there is provided an imaging system comprising the above imaging device connectable to a computer device.

Preferably, the transceivers are sequentially operated, so as to significantly simplify the image processing. To this end, the control unit comprises a synchronizer block for operating a power supply of the transceivers accordingly. First, the transceivers of the first group are sequentially activated to irradiate the plurality of areas within a slice and generate data indicative thereof. This data is stored in a memory of the computer device, until all other groups of the transceivers are sequentially operated, and then used by a suitable software application for providing a 3D image of the entire structure covered by the cover.

Thus, according to yet another aspect of the present invention, there is provided an imaging method for obtaining a three-dimensional image of an internal structure of a body part utilizing an imaging device having a cover for covering said body part and carrying at least two groups of ultrasonic transceivers, wherein an overlap exists between areas irradiated by each two locally adjacent transceivers I the group, the method comprising the steps of:

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1A:
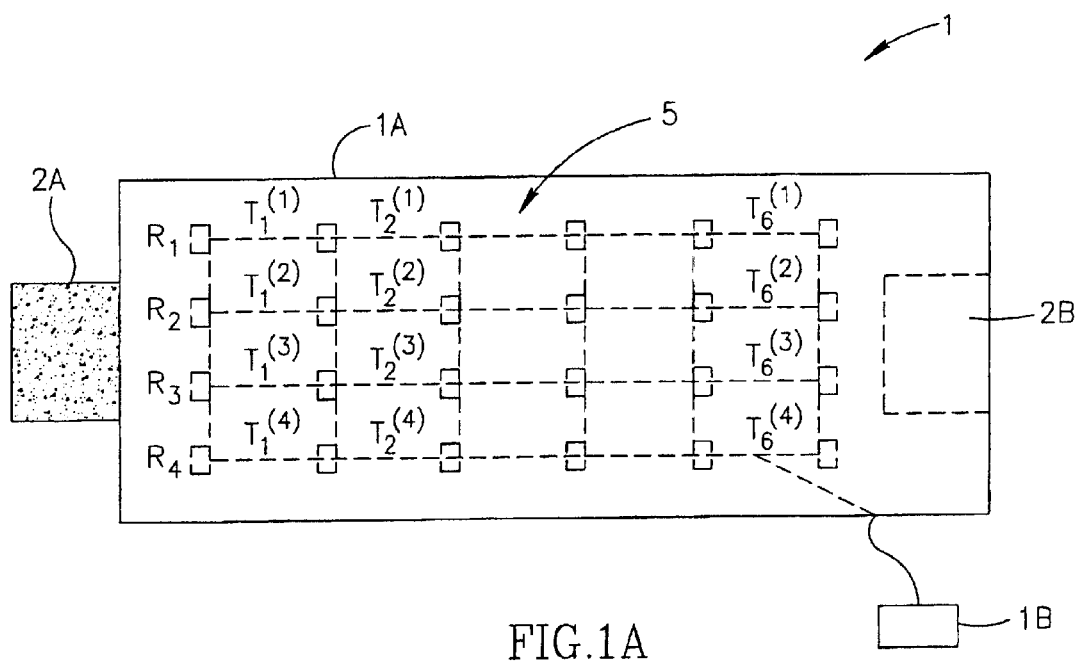
FIGS. 1a and 1b schematically illustrate one example of an imaging device according to the present invention.
Figure 1B:
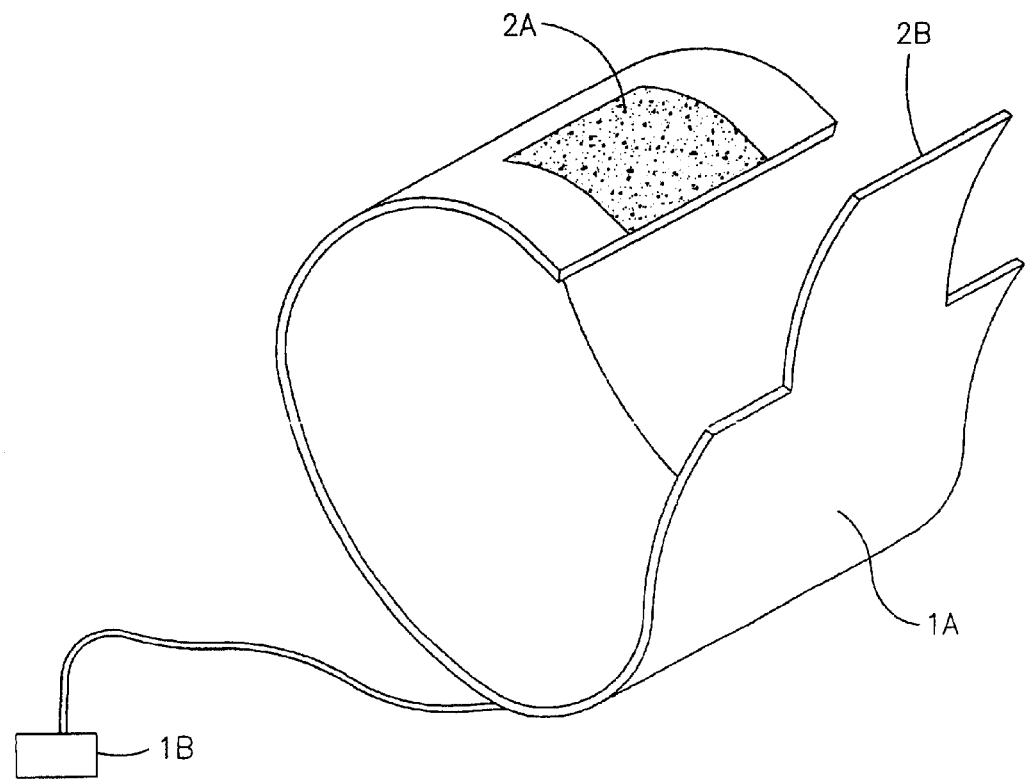

Referring to FIGS. 1a and 1b, there is schematically illustrated an imaging device 1 constructed and operated according to the invention. The device 1 is composed of a light elastic cover 1A associated with a control unit 1B (adaptor). The cover 1A, when in an inoperative position thereof (FIG. 1a) is a strap formed with two connectors 2A and 2B (e.g., Velcro fasteners) at its opposite ends, so as to form an open sleeve (FIG. 1b) capable of wrapping a patient's organ (not shown here) when in the operative position of the device. The sleeve resembles a sphygmomanometer cuff, being made of several layers of cloth or other flexible material. The sleeve is easy to wear and can be adapted to a wide range of limbs of various sizes.

Mounted on the strap 1A (i.e., built-in between the layers) is a two-dimensional array of transceivers, generally designated as 5, each transceiver being composed of a piezoelectric transducer and a receiver for, respectively, transmitting and receiving ultrasonic waves. In the present example, the 2D array 5 is formed by four parallel spaced-apart groups (rows) $R_1$–$R_4$ extending along the strap 1A, each group including six transceivers aligned in a spaced-apart relationship. As shown, transceivers $T_1^{(1)}$–$T_6^{(1)}$ form the group $R_1$, transceivers $T_1^{(2)}$–$T_6^{(2)}$ form the group $R_2$, etc.

It should be noted, although not specifically shown that the control unit 1B comprises such main constructional parts as a power source for electrically operating the transducers, and a synchronizer block, the purpose of which will be described further below.

Figure 2:
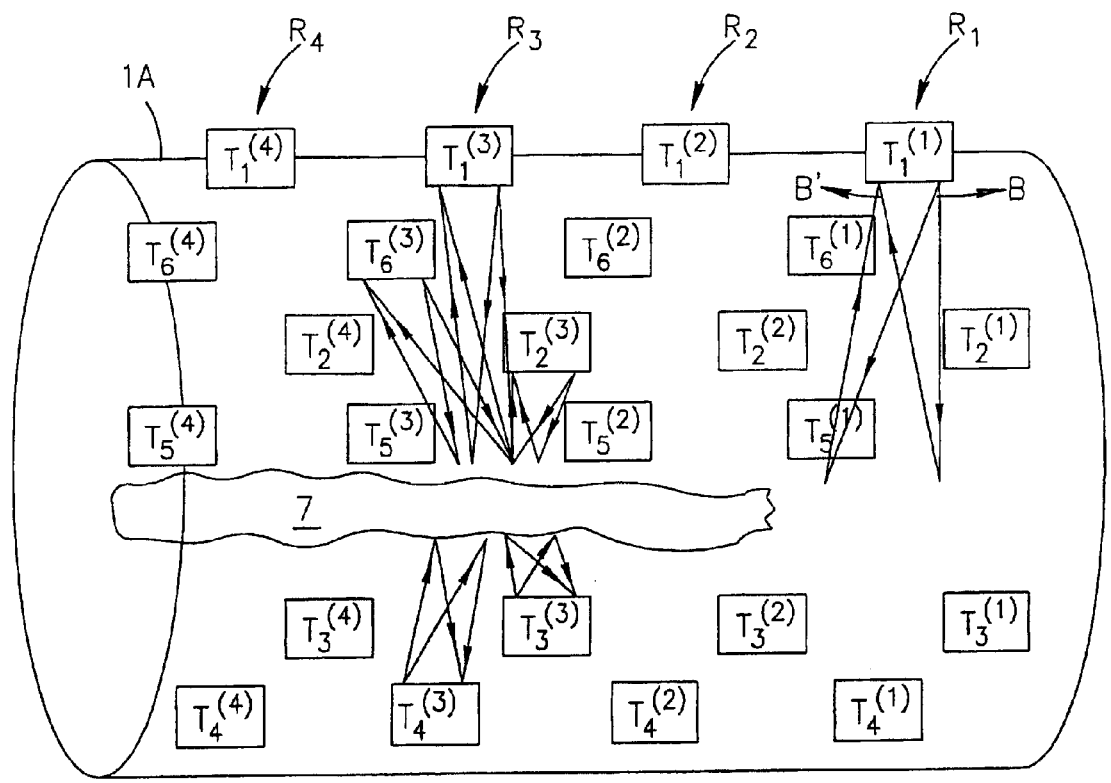
FIG. 2 more specifically illustrate an arrangement of transceivers when in an operational position of the device of FIGS. 1a–1b.

As better shown in FIG. 2, when rolling the strap 1 into its operational position forming an open sleeve (for placing the device onto a patient's organ, such as his limb), the transceivers of each row become arranged along the circumferential region of the sleeve, thereby forming a circular array around the patient's limb.

The operation of the transceivers of each group enables the creation of a 360-degree section of the limb under examination. Each of the transceivers emits a beam B (solid angle) of ultrasonic radiation (wave) propagating towards an area located within a region to be imaged, and receives a signal response B' of this area. This is exemplified in the figure in a self-explanatory manner with respect to the transceiver $T_1^{(1)}$, $T_1^{(3)}$–$T_6^{(3)}$. As also shown in the figure, the transceivers in each row are spaced from each other such that the beams emitted by two locally adjacent transceivers provides a certain overlap between the irradiated areas. Generally speaking, each two locally adjacent transceivers in the group enables the stereoscopic imaging of the same location (overlapped region).

Figure 3:
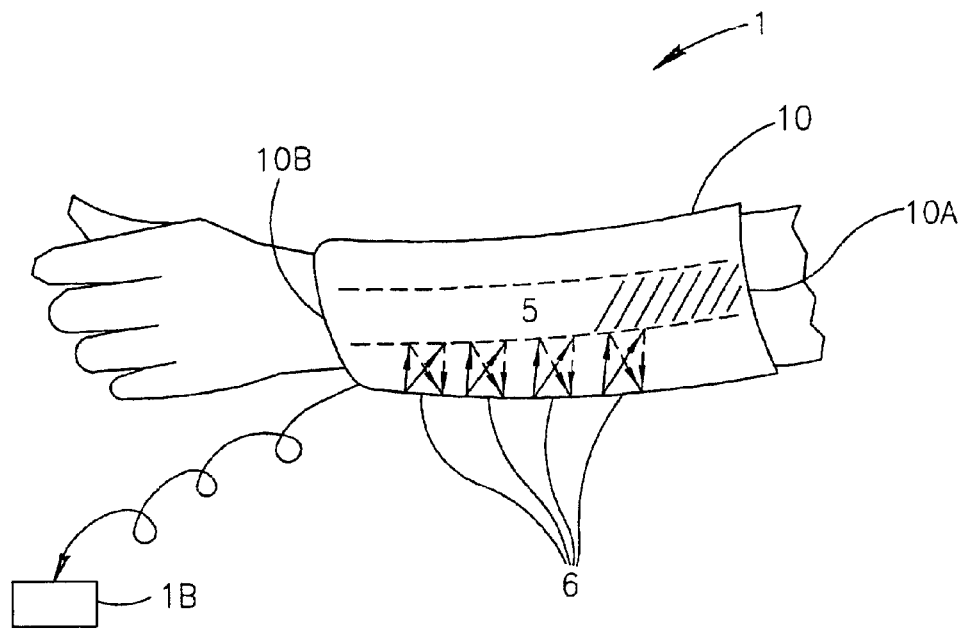
FIG. 3 is a schematic illustration of an imaging device according to another example of the present invention.

FIG. 3 illustrates the device 1 in operation, being worn by a patient on his arm. In this example, the strap 1A of FIGS. 1a–1b is replaced by an elastic cuff (the so-called "close sleeve") 10, which is open at both ends 10A and 10B, so as to be placed on the patient's extreme organ, without the need for any fasteners.

Turning back to FIG. 2, the operation of all the transceivers in the group creates a plurality of imaging sectors, thereby enabling the creation of a 360-degree section. The provision of at least two groups of transceivers enables simultaneous (i.e., at the same current position of the device with respect to the patient's organ) imaging of two such 360-degree sections, which may be processed by a suitable image processing technique to reconstruct a 3D image of the internal structure of the patient's organ covered by the sleeve.

The above construction of the imaging device enables to maintain the distances between the transceivers, and the transceivers and the region to be imaged. Accordingly, movements, position shifts and the involuntary tremor of the patient do not affect the course of the examination. This makes the device suitable for examining babies and children. Moreover, the sleeve structure of the device solves the problem of repeat examination. Indeed, since the relative location of the transceivers does not change (neither relative to themselves nor relative to the body part under examination), the examination conditions are identical in all respects and enable true comparison. The flexibility and mobility of the sleeve eliminate the need to move the patient's body, or the limb under examination. The sleeve is simply placed around the body part to be examined (e.g., supposedly damaged part). This makes the device suitable for field casualties and road accidents, when the extent and severity of the internal injuries are not known.

Figure 4:
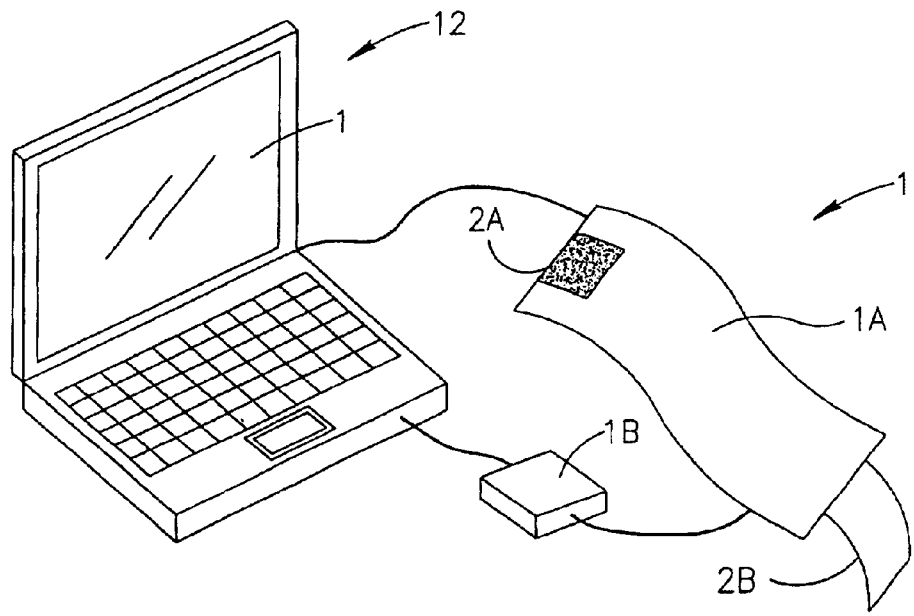
FIG. 4 is a schematic illustration of an imaging system utilizing the imaging device of the present invention.

FIG. 4 illustrates an imaging system composed of the imaging device 1 connected to a conventional computer device (laptop) 12 installed with a suitable software application, which is capable of collecting and processing data generated by the device 1.

As indicated above, the control unit 1B (FIG. 1a) includes the synchronizer block (i.e. a timing system) that operates the power source so as to provide a sequential imaging. More specifically, each transceiver (composed of a transmitter and receiver) transmits and receives ultrasonic waves within a given time, and generates data indicative of the received signal. This data is transmitted to a storage utility (database or memory) in the computer device 12. The synchronizer block operates the power supply to sequentially operate all the transceivers in the first group $R_1$ (six transceivers in the present example), and data indicative of an acoustic response of all the imaged areas are transmitted to the storage utility. Then, an image processing utility (a suitable software application) installed in the computer device operates to build an image of the first section (using the previously stored data). In the same way, the software application processes data generated by the transceivers of the groups $R_2$, $R_3$ and $R_4$ collected in a sequential manner.

Hence, information about the four image sections is created and stored in the memory of the computer device. At a next operational step, a 3D image is constructed using the stored information on the four sections, and the image is displayed on a monitor of the computer device. This sequence of operations is fast enough to generate a continuous flow of 3D images of the sections, in order to create the illusion of motion in real time (if any) within the organ/limb under examination.

Thus, the technique of the present invention provides the creation of a three dimensional image (picture) of an internal structure of an organ from a series of slice images, each of the slice images being in the form of a 360-degree section image.

It should be noted that if some of the transceivers overlap when wrapping the strap around the patient's organ, the system will disregards the uppermost of the overlapping receivers. This is determined during self-calibration of the system.

It should also be noted that data indicative of a constructed image may be transmitted from the computer 12 to a central medical station through a computer network. Alternatively, the control unit of the imaging device may include a suitable communication utility for transmitting the collected data to the central station through a telephone communication link.

Figure 5:
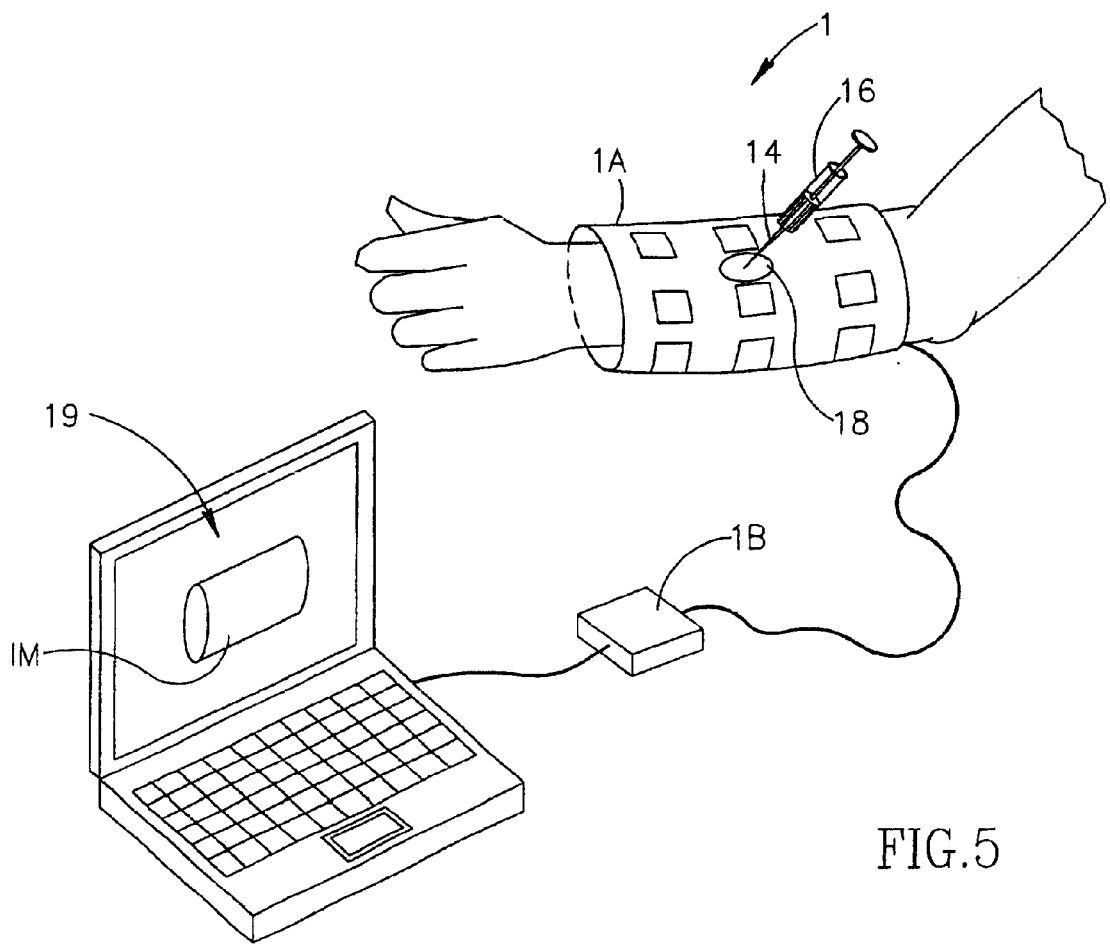
FIG. 5 shows the imaging device of the present invention applied to locate the patient's blood vessels and to guide a needle of a syringe towards the patient's vein.

Referring to FIG. 5, there is illustrated an example of applying the imaging device 1 of the present invention to locate the patient's blood vessels and to guide a needle 14 of a syringe 16 towards the patient's vein via an aperture 18 provided in the sleeve 1A., while continuously imaging the structure of the veins of the patient. A 3D image IM of the structure is displayed on the computer's monitor 19 showing the needle and vein (which are not illustrated here). Such a device is particularly useful when the veins of the patient are hidden, and may be regularly used in hospitals for setting an infusion system or any other treatment, for the convenience of the patient and the nurse.

It should be noted, although not specifically shown, that the sleeve may include an inner disposable sterile element.

Figure 6:
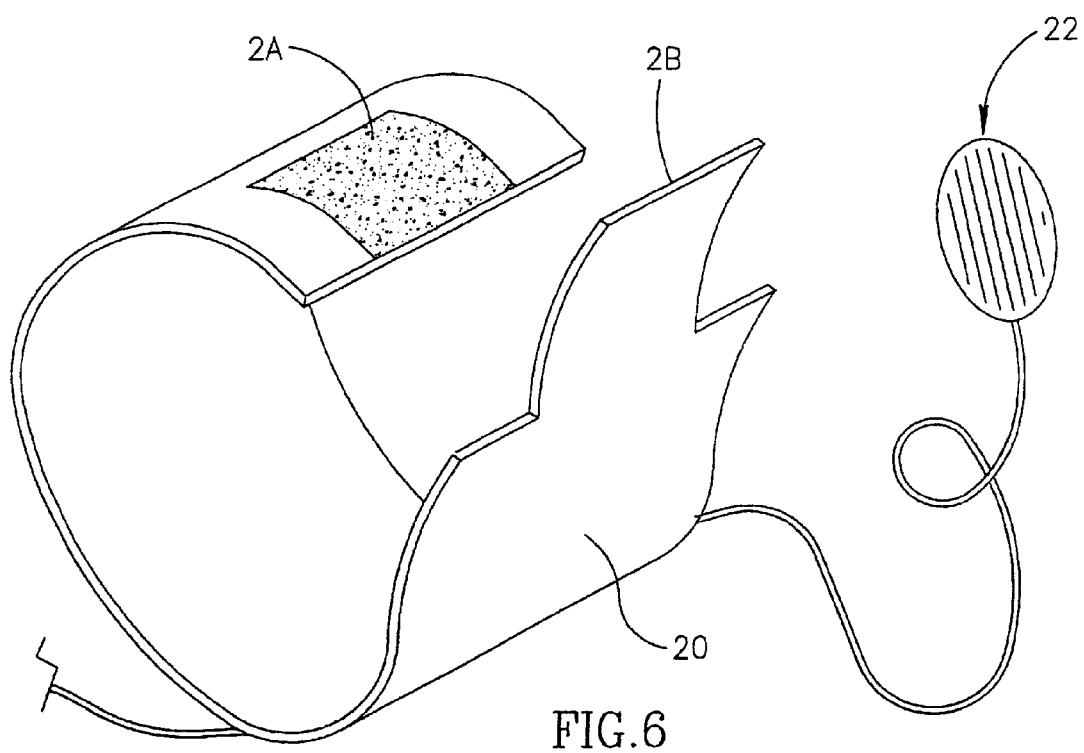
FIG. 6 illustrates yet another example of an imaging device of the present invention utilizing an inflatable cover for covering a body part to be imaged.

As shown in the example of FIG. 6. a sleeve 20 may be inflatable. To this end, the sleeve 20 is constructed generally similar to the above described sleeve 1A (FIGS. 1a–1b) or sleeve 10 (FIG. 3), but is additionally provided with a hollow layer that enables the introduction of air (inflation) by means of a conventional pneumatic assembly (pump) 22 typically used with a sphygmomanometer cuff.

Figure 7:
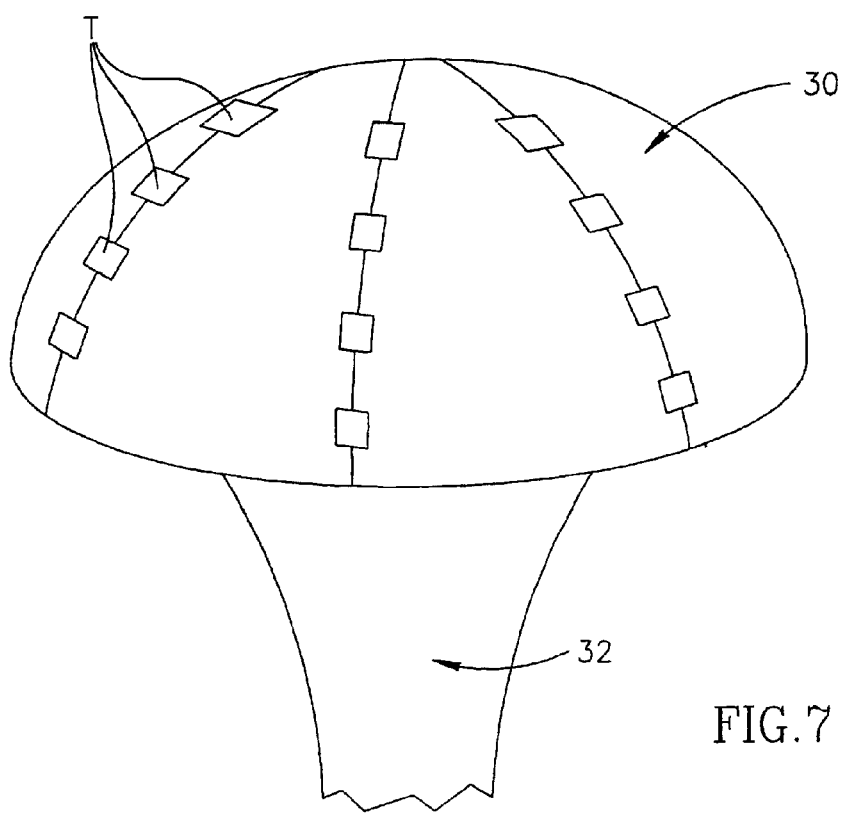
FIG. 7 illustrates an imaging device of the present invention designed to be uses for monitoring a woman's abdomen.

According to another example of the present invention shown in FIG. 7, an elastic cover of the imaging device is in the form of a dome-shape open sleeve (cup) 30 adapted to cover the abdominal portion of a pregnant woman or a woman's breast. Cup 30 is made of a substantially flexible/elastic material which adapts to the varying sizes and, when intended for covering the woman's abdomen, is formed with strips 32 for tying behind the back and securing the cup. This enables to achieve the optimum positioning of sensors (transceivers), generally at T, which are in the present example arranged in several groups, extending radially from the top of the cup.

Those skilled in the art will readily appreciate that various modifications and changes can be applied to the embodiments of the invention as hereinbefore exemplified, without departing from its scope defined in and by the appended claims.

What is claimed is:

1. An imaging device for monitoring a body part and generating data indicative of a three-dimensional image of an internal structure of the body part, the device comprising:

(i) a substantially elastic cover for covering the body part when in an operative position of the device (ii) a control unit coupled to the cover;

(iii) an array of ultrasonic transceivers mounted on the cover each for emitting a beam of ultrasonic waves for irradiating an area within a region covered by the cover, and for detecting a signal response of the irradiated area, the array of the transceivers being composed of at least two spaced-apart parallel groups of the transceivers, wherein the transceivers of each group are arranged in a spaced-apart relationship, and the space between each two adjacent transceivers in the group is such that an overlap exists between the areas irradiated by the adjacent transceivers.

2. The device according to claim 1, wherein the cover, when in an inoperative position thereof, is in the form of a strap provided with two fasteners at its opposite ends for securing the cover on the body part when wrapped by the cover, while in the operational position thereof.

3. The device according to claim 1, wherein the cover is in the form of a sleeve open at opposite ends thereof so as to be put onto the body part.

4. The device according to claim 1, wherein the cover, when in an inoperative position thereof is in the form of a circle capable of forming a spherical part, when in the operative position of the cover.

5. The device according to claim 1, wherein each of the transceivers comprises a piezoelectric transducer.

6. The device according to claim 1, wherein said cover is formed with an inner disposable layer contacting the surface of the body during the operation of the device.

7. The device according to claim 1, wherein the control unit comprises a power source for activating the transceivers, and a synchronizer block for sequentially operating the transceivers.

8. An imaging system comprising an imaging device for monitoring a body part and generating data indicative of a three-dimensional image of an internal structure of the body part, a control unit for operating the imaging device, and a computer device connectable to the imaging device for processing data generated by the imaging device and constructing and displaying said three-dimensional image, wherein the imaging device comprises:

(i) a-substantially elastic cover for covering the body part when in an operative position of the device;

(ii) a control unit coupled to the cover;

(iii) an array of ultrasonic transceivers mounted on the cover each for emitting a beam of ultrasonic waves for irradiating an area within a region covered by the cover, and for detecting a signal response of the irradiated area, the array of the transceivers being composed of at least two spaced-apart parallel groups of the transceivers, wherein the transceivers of each group are arranged in a spaced-apart relationship, and the space between each two adjacent transceivers in the group is such that an overlap exists between the areas irradiated by the adjacent transceivers.

9. An imaging method for obtaining a three-dimensional image of an internal structure of a body part utilizing an imaging device having a cover for covering said body part and carrying at least two groups of ultrasonic transceivers, wherein an overlap exists between areas irradiated by each two locally adjacent transceivers in the group, the method comprising the steps of:

(a) sequentially operating each of the transceivers in one group for irradiating corresponding areas within a region covered by the cover, and generating data indicative of 360-degree section of the body part;

(b) repeating step (a) with respect to at least one other group of the transceivers, so as to generate data indicative of at least one further 360-degree section; and (c) processing the generated data to construct said three-dimensional image of the internal structure of the body part.

* * * * *